US012765834B2

(12) United States Patent
Ruggeri et al.

(10) Patent No.: US 12,765,834 B2
(45) Date of Patent: Oct. 20, 2026

(54) PERFUSION DEVICE FOR EVALUATING BLOOD PARAMETERS

(71) Applicant: SEDICIDODICI S.R.L., Pordenone (IT)

(72) Inventors: Zaverio M. Ruggeri, Pordenone (IT); Angelo Manzoni, Pordenone (IT); Noemi Vanerio, Pordenone (IT); Mario Mazzucato, Concordia Sagittaria (IT)

(73) Assignee: SEDICIDODICI S.R.L., Pordenone (IT)

(*) Notice: Subject to any disclaimer, the term of this patent is extended or adjusted under 35 U.S.C. 154(b) by 633 days.

(21) Appl. No.: 18/258,745

(22) PCT Filed: Nov. 3, 2021

(86) PCT No.: PCT/IB2021/060167
§ 371 (c)(1),
(2) Date: Jun. 21, 2023

(87) PCT Pub. No.: WO2022/136960
PCT Pub. Date: Jun. 30, 2022

(65) Prior Publication Data
US 2024/0050033 A1 Feb. 15, 2024

(30) Foreign Application Priority Data
Dec. 21, 2020 (IT) ........................ 102020000031580

(51) Int. Cl.
*A61B 5/00* (2006.01)
*B01L 3/00* (2006.01)
*G01N 33/49* (2006.01)

(52) U.S. Cl.
CPC ...... *A61B 5/4836* (2013.01); *B01L 3/502715* (2013.01); *B01L 3/502746* (2013.01);
(Continued)

(58) Field of Classification Search
CPC ................................................ G01N 33/4905
See application file for complete search history.

(56) References Cited

U.S. PATENT DOCUMENTS

2007/0172389 A1 7/2007 Wilding et al.
2015/0025348 A1 1/2015 Grabowski
(Continued)

FOREIGN PATENT DOCUMENTS

EP 1636595 B1 * 10/2008 ......... G01N 33/4905
EP 2010903 A1 1/2009
(Continued)

OTHER PUBLICATIONS

International Search Report and Written Opinion for PCT/IB2021/060167 (Jan. 25, 2022).

*Primary Examiner* — Kathryn Elizabeth Limbaugh
(74) *Attorney, Agent, or Firm* — Merchant & Gould P.C.

(57) ABSTRACT

A perfusion device is for evaluating the risk of thrombotic and hemorrhagic diseases linked to blood coagulation processes. In particular, a cartridge is for conducting a dynamic "ex-vivo" evaluation method of the coagulation process in a subject's blood sample, including at least one perfusion chamber, a well for loading the blood sample and reagents, an inclined ascending microchannel connecting the well to a first end of the perfusion chamber and an inclined descending microchannel placed at a second end. Preferably at least one perfusion chamber includes two half-channels of different width, placed in series or in parallel, or the cartridge includes at least two perfusion chambers placed in parallel. At least two of the perfusion chambers have a different width.

18 Claims, 6 Drawing Sheets

(52) U.S. Cl.
CPC .. *G01N 33/4905* (2013.01); *B01L 2300/0636* (2013.01); *B01L 2300/0822* (2013.01); *B01L 2300/0864* (2013.01); *B01L 2300/0874* (2013.01); *B01L 2300/0877* (2013.01); *B01L 2400/0478* (2013.01); *B01L 2400/049* (2013.01)

(56) References Cited

U.S. PATENT DOCUMENTS

| | | | | |
|---|---|---|---|---|
| 2016/0334612 | A1* | 11/2016 | Stoecker ................ | G02B 21/34 |
| 2017/0261737 | A1 | 9/2017 | Sakamoto et al. | |
| 2018/0169657 | A1* | 6/2018 | Kelly ..................... | C12M 23/58 |

FOREIGN PATENT DOCUMENTS

| | | | |
|---|---|---|---|
| EP | 2228657 | A1 | 9/2010 |
| EP | 2817099 | A2 | 12/2014 |
| WO | 2006/057028 | A1 | 6/2006 |
| WO | 2007/068727 | A1 | 6/2007 |
| WO | 2013/124727 | A2 | 8/2013 |

* cited by examiner

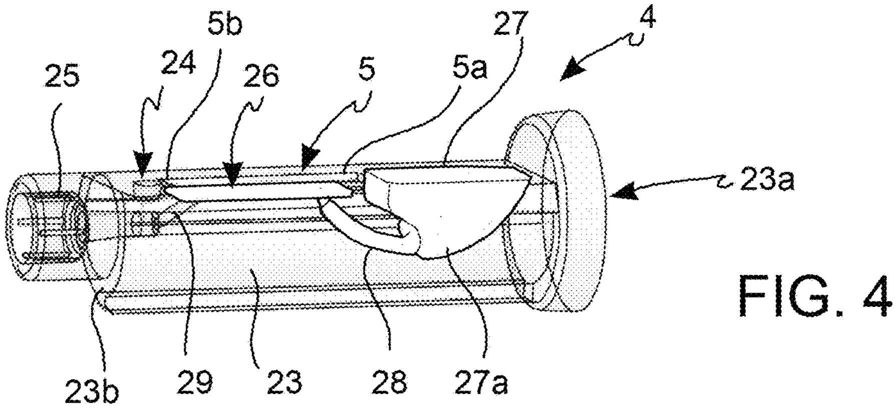
FIG. 4
FIG. 5
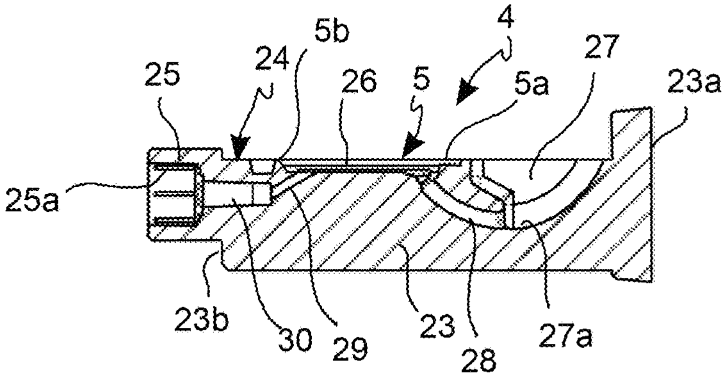
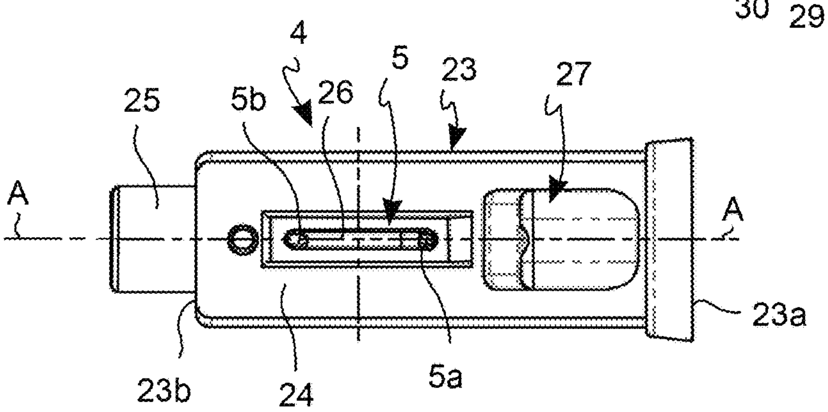
FIG. 6
FIG. 7
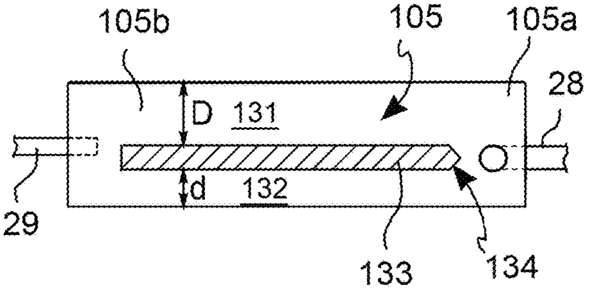

PERFUSION DEVICE FOR EVALUATING BLOOD PARAMETERS

This application is a National Stage Application of PCT/IB2021/060167, filed Nov. 3, 2021, which claims benefit of priority to Application No. 102020000031580, filed Dec. 21, 2020 in Italy, and which applications are incorporated herein by reference. To the extent appropriate, a claim of priority is made to each of the above-disclosed applications.

TECHNICAL FIELD OF THE INVENTION

The object of the present invention is a perfusion device for a method for evaluating the risk of thrombotic and hemorrhagic diseases linked to blood coagulation processes, such as hemophilia or thrombosis, as well as for monitoring pharmacological therapies.

BACKGROUND ART

The coagulation of blood is a complex, multifactorial physiological process which allows the body to respond to a thrombogenic stimulus (e.g., the lesion of a vessel). The coagulation process is a physiological mechanism which leads to the repair of damaged blood vessels and is essential to avoid bleeding in the case of vascular lesions of any nature.

Coagulation comprises a vascular and platelet phase (primary hemostasis) and a coagulation phase (secondary hemostasis).

The formation of a hemostatic clot at a vascular lesion is a physiological process. In healthy individuals, it occurs by virtue of the adhesion and aggregation capacity of platelets (primary hemostasis), the activation of which leads to the formation of an aggregate which, by virtue of fibrin formation (secondary hemostasis), then forms a hemostatic plug which allows stopping the outflow of blood from the lesion itself.

If blood coagulation is abnormal in the "excessive" sense, thrombotic diseases arise, if it is "poor", hemorrhagic diseases arise.

Thrombosis is a pathological process which consists in the non-physiological formation of one or more blood clots called thrombi, consisting of fibrin, platelets, red blood cells and white blood cells. When, due to abnormalities of the coagulation process or because of external agents (such as the presence of a cholesterol plaque which reduces the lumen of the vessel), the thrombus obstructs or limits the normal blood supply to the involved organ, the patient is at risk of acute phenomena such as thrombosis, myocardial infarctions, ischemic strokes, pulmonary embolisms. Among the thrombotic diseases we mention, firstly, all the chronic or acute diseases which fall under the name of cardiovascular diseases (CVDs).

In hemorrhagic diseases, on the contrary, the alteration of the coagulation process is ineffective and leads to the appearance of hemorrhagic events. This is the case, for example, of factorial deficits, of Von Willebrand's disease, of hemophilia, etc.

For years, some technological limitations have prevented the diagnosis of coagulation deficits in individuals suffering from hemostatic disorders. Similarly, it is extremely difficult to determine how these deficits can be related to similar thrombogenic disorders with which they synergize, causing severe physio-pathological dysfunctions.

A relevant problem lies in the fact that said pathological manifestations are difficult to diagnose as they are silent, or present also in subjects who in normal life have never shown pathological events and who in the occasion of "traumatic" events, such as surgery, incur severe hemorrhagic or thrombotic-ischemic manifestations.

Another relevant problem is the monitoring of antiplatelet or anticoagulant pharmacological treatments, so as to be able to evaluate the effectiveness of such treatments over time.

There is therefore a need, in the clinical setting, for an "ex vivo" functional test which allows identifying potential thrombotic or hemorrhagic risks.

The methods used today for the diagnostic analysis of blood coagulation dysfunctions can be divided into three categories: i) methods which evaluate only platelet function as a whole, ii) methods which define the features of only the plasma component of the blood, iii) methods which evaluate coagulation as a whole using whole blood, without distinguishing platelet function from fibrin component.

Information on platelet function is currently acquired through aggregation tests, while the function of the plasma component is established through the determination of prothrombin time (PT) and partial thromboplastin time (aPTT) which analyze the extrinsic and intrinsic coagulation cascade of blood coagulation, respectively.

It is common clinical practice to consider both cascades because both converge in factor X (tenth) which mediates the conversion of prothrombin to thrombin, which is the ultimate factor responsible for the conversion of fibrinogen to fibrin. However, the analyses of these two cascades do not allow us to understand, for example, why patients with factor XII congenital deficiency do not have alterations in coagulation, while defects in factor IX activity define a particularly critical clinical picture.

"Ex vivo" dynamic evaluation methods of the coagulation phenomenon are known from European patent application 06819957.9 and from the international application published under no. WO 2013/124727, both in the name of the Applicant. Such patent applications describe a method and an apparatus for the dynamic determination of the formation of platelet aggregates in a patient's blood sample.

The present invention stems from the consideration that in both physiological and pathological conditions, the thrombus formation is initiated by flow interactions between platelets, plasma components and the damaged vessel wall.

The combination of adhesion, activation and platelet aggregation, together with the components of the extracellular matrix (ECM) present in the sub-endothelium and the concomitant coagulation process triggered in the vascular lesion site by the exposure of the subendothelial tissue factor, lead to the formation of fibrin, which stabilizes the platelet thrombus.

Therefore, the inventors of the present patent application have come to the conclusion that an "ex-vivo" clinical determination method must concern a dynamic and non-static analysis of a multifactorial process and must take into account the main cellular and molecular mechanisms which modulate platelet aggregation and adhesion, as well as thrombin generation and fibrin formation.

To this end, it is essential to provide a cartridge comprising one or more perfusion chambers which allows the execution of the method outlined above.

SUMMARY OF THE INVENTION

Therefore, the present invention relates to a cartridge comprising one or more perfusion chambers for carrying out an "ex-vivo" dynamic evaluation of the coagulation process in a subject's blood sample, as outlined in the appended claims, the definitions of which form an integral part of the present description for the purposes of description sufficiency.

Another aspect of the present invention is an apparatus for the "ex-vivo" dynamic evaluation of the coagulation process in a subject's blood sample.

The present invention further relates to a software for the digital image processing which is usable with an apparatus for the "ex-vivo" dynamic evaluation of the coagulation process in a subject's blood sample.

Further objects, features and advantages of the invention will become apparent from the following description of preferred embodiments thereof, given by way of indicative and non-limiting examples.

BRIEF DESCRIPTION OF THE DRAWINGS

FIG. 4 depicts a perspective view in transparency of an analysis cartridge;

FIG. 5 depicts a longitudinal sectional view of the cartridge of FIG. 4;

FIG. 6 depicts a top plan view of the cartridge of FIG. 4;

FIG. 7 depicts a top plan view of an embodiment of the perfusion chamber of the cartridge of FIG. 4;

DETAILED DESCRIPTION OF THE INVENTION

Figure 1:
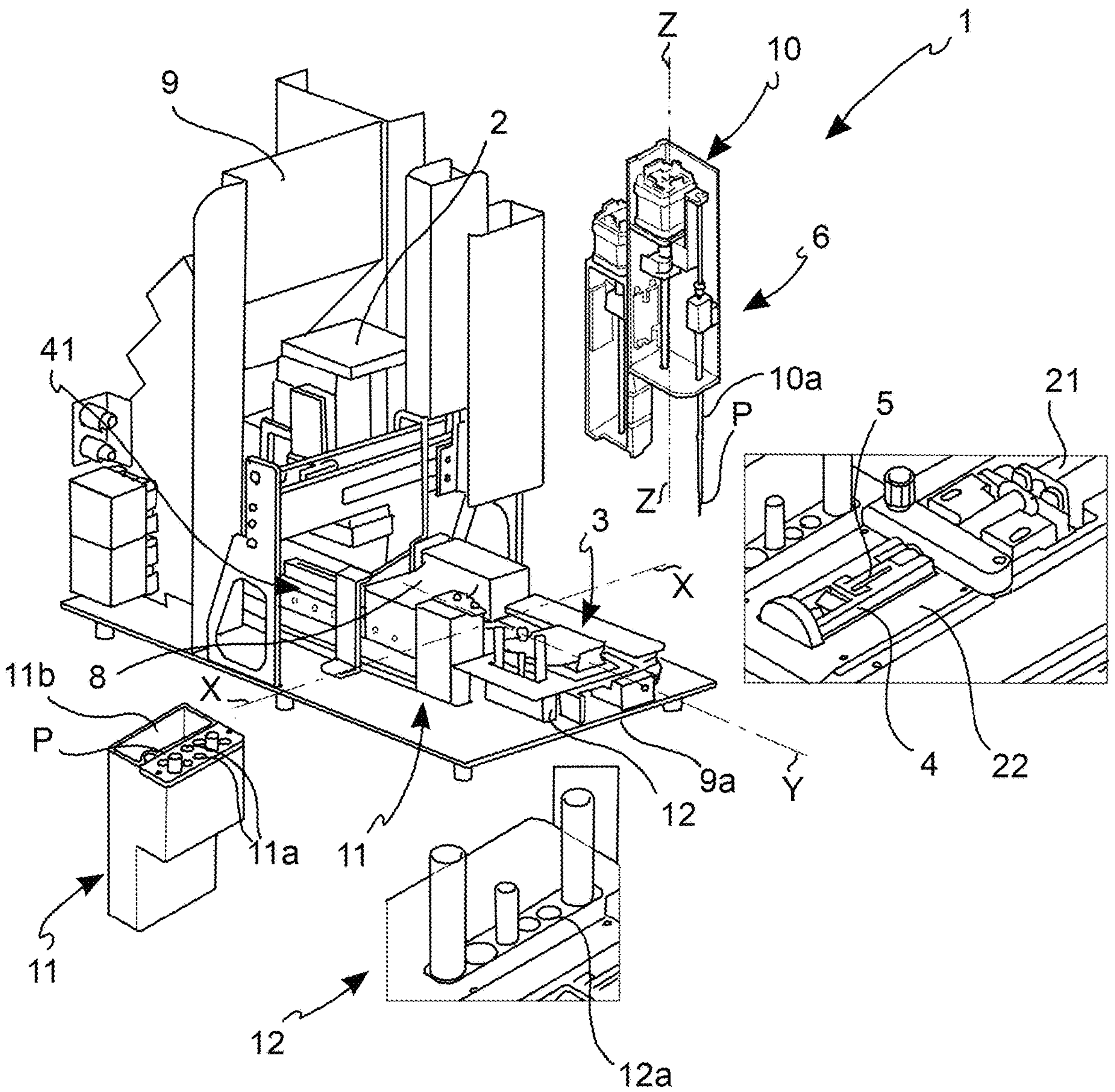
FIG. 1 depicts a partial perspective view of the apparatus according to the invention and, in enlargement, of some details of said apparatus.

The present invention firstly relates to a method for the dynamic "ex-vivo" evaluation of the coagulation process in a patient's blood sample, characterized in that such a method comprises the simultaneous determination on the same blood sample of both the time, quantity and speed of platelet aggregate formation and of fibrin formation time, quantity and speed.

According to some embodiments, the method of the invention comprises the following steps:

a) providing a whole-blood sample taken from a subject and added with an anti-coagulant substance;

b) treating the blood sample of step a) with a solution consisting of fluorescent probes for marking platelets and fibrin capable of binding more or less specifically to platelets and fibrin and emitting fluorescent light on two different emission frequencies and of a recalcification solution of the blood sample. The two aforesaid solutions can also be combined in a single solution or single reagent;

c) introducing said recalcified blood sample into an analytical device having at least one perfusion chamber, in which at least one wall consists of a transparent material comprising a cytoadhesive substance, the blood sample being made to flow into the perfusion chamber in known and measurable flow conditions;

d) during the blood flow in the perfusion chamber, alternately acquiring at least two series of fluorescence images, so that at least one series of fluorescence images is acquired at an emission wavelength characteristic of the fluorescent probe for platelets and at least one other series of fluorescence images is acquired at another emission wavelength characteristic of the fluorescent probe for fibrin;

e) binarizing the pixels of the acquired images for the platelets and for the fibrin, so as to generate a first curve of area covered by illuminated pixels vs. time (t) for the formation of a platelet aggregate and a second curve of area covered by illuminated pixels vs. time for the fibrin formation;

f) generating a first curve of average fluorescence intensity vs. time for the formation of the platelet aggregate and a second curve of average fluorescence intensity vs. time for the fibrin formation;

in which the method comprises at least one of the following steps:

g) generating a first integrated density curve defined as the product of area and fluorescence intensity vs. time for the formation of the platelet aggregate and a second integrated density curve defined as the product of area and fluorescence intensity vs. time for the fibrin formation;

h) generating a curve of particle number vs. time, in which the number of particles is given by the number of platelet aggregates consisting of more than 2 illuminated pixels;

i) generating a curve of particle size vs. time, in which the particle size is given by the average size of the platelet aggregates consisting of more than 2 illuminated pixels;

j) generating values of maximum slope, defined as the relative maximum points of the first derivative function calculated for the curves of the parameter obtained in said at least one step e), f), g), h) and i);

k) generating values of maximum acceleration, defined as the relative maximum points of the second derivative function calculated for the curves of the parameter obtained in said at least one step e), f), g), h) and i);

l) generating values of F/P ratio, defined as the ratio of the AUCs of fibrin to the AUCs of the platelets of the parameter obtained in said at least one step e), f) and g);

the method further comprising the steps of:

m) generating a lag time value representing the fibrin formation time defined as the time corresponding to the first occurrence of five consecutive images in which the value of the measured area related to fibrin is >1% of the maximum peak value of the curve;

n) generating AUC (Area Under the Curve) values given by the area under the curve of each parameter obtained in steps e), f), g), h) and i).

The blood sample used in step a) is a human or animal blood sample, preferably human blood. For example, a venous blood sample can be used without blood extravasation, ruptures of veins or similar events. The blood is added with an anti-coagulant until it is used in the method of the invention, to avoid triggering coagulation phenomena. Suitable anti-coagulant substances used for such a purpose are, for example, heparin or salts of citric acid.

In certain embodiments, the fluorescent probes used in step b) are:

for marking platelets, the quinacrine probe having an excitation wavelength of about 488 nm and an emission wavelength of about 510 nm, with the formula:

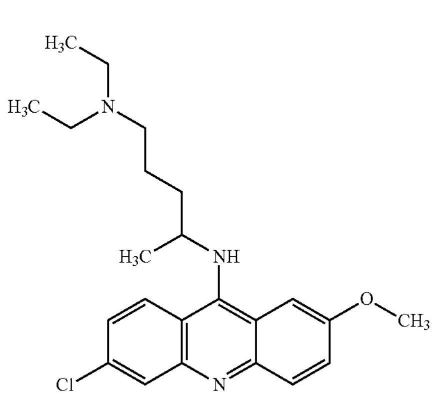 [SMILES: CCN(CC)CCCC(C)Nc1c2ccc(Cl)cc2nc2ccc(OC)cc12]

or an antiplatelet antibody or a derivative thereof (e.g., Fab, antigen-binding fragment), conjugated with a fluorescent molecule (ALEXA Fluor® 488) having an excitation wavelength of about 495 nm and an emission wavelength of about 519 nm, with the formula:

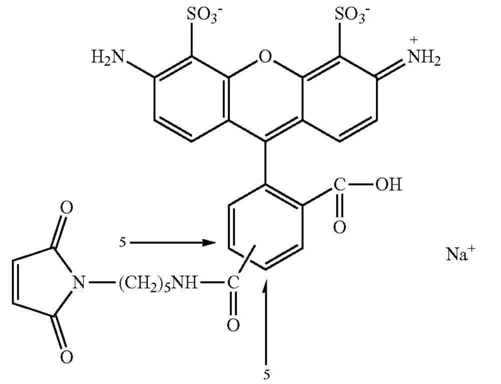

for marking fibrin, an antifibrin antibody conjugated with a fluorescent molecule, (ALEXA Fluor® 546), having an excitation wavelength of about 556 nm and an emission wavelength of about 573 nm, with the formula:

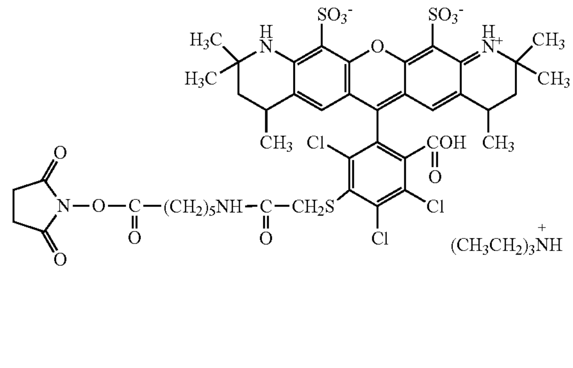

Step b) is carried out by adding a predetermined quantity of a fluorescent probe for platelets and a fluorescent probe for fibrin to the blood sample. The reagents can be added in liquid form or in alternative forms, for example as a lyophilized powder to which the blood sample is added.

The fluorescent probes can be injected "pure" into the sample or linked to other specific markers (e.g., antibodies).

In preferred embodiments, the fluorescent probes are those described above and are added to the blood sample obtaining a probe concentration between 8 μM and 11 μM, preferably between 9 μM and 10 μM, for quinacrine, between 17 μg/mL and 20 μg/mL preferably between 18 μg/mL and 19 μg/mL for antifibrin antibody and between 1.5 μg/mL and 3.5 μg/mL preferably between 2 μg/mL and 3 μg/mL for antiplatelet antibody. For example, the fluorescent probes can be added in the following ratios:

7 μL of quinacrine for 806 μL of blood (final quinacrine concentration 10 μM) for a low shear rate test and 17 μL of quinacrine for 2950 μL of blood (final quinacrine concentration 10 μM) for a high shear rate test;

13.5 μL of marked antiplatelet antibody per 1000 μL of blood (final antibody concentration 2.6 μg/mL) for a low shear rate test and optionally 67.5 μL of marked antiplatelet antibody per 5000 μL of blood (final antibody concentration 2.6 μg/mL) for a high shear rate test.

13.5 μL of marked antifibrin antibody per 1000 μl of blood (final antibody concentration 18.6 μg/mL) for a low shear rate test and optionally 67.5 μL of marked antifibrin antibody per 5000 μL of blood (final antibody concentration 18.6 μg/mL) for a high shear rate test.

The recalcification of the blood sample included in step b) allows reactivating the coagulation process.

The recalcification of the blood sample is carried out by adding a suitable quantity of calcium salt, preferably calcium chloride. In preferred embodiments, calcium chloride is added in quantities of about 13.5 μL of 800 mM solution per 1000 μL of blood in a low shear rate test and in quantities of about 67.5 μL of 800 mM solution per 5000 μL of blood in a high shear rate test. In an embodiment the volume ratio of single reagent to blood is about 1:20, where the single reagent is a solution of marked antiplatelet antibody, marked antifibrin antibody and calcium chloride.

The time between recalcification and injection in the analytical device is short and controlled to prevent the coagulation process from starting before the blood sample enters the perfusion chamber.

As will be better described hereafter, the injection of the blood sample is preferably carried out by an automatic pipettor, while the perfusion is preferably carried out by a syringe pump placed downstream of the perfusion chamber, thus operating in aspiration mode.

In an embodiment, the blood sample flows in the perfusion chamber, which comprises at least one microchannel section configured so as to obtain a shear rate between 150 $sec^{-1}$ and 500 $sec^{-1}$, preferably about 300 $sec^{-1}$ to simulate the physiological conditions in the venous vessels, and at least one microchannel section configured so as to obtain a shear rate between 1000 $sec^{-1}$ and 2000 $sec^{-1}$, preferably about 1500 $sec^{-1}$, to simulate the physiological conditions in the arterial vessels.

In other embodiments, it is possible to use a perfusion chamber having a single microchannel section, repeating the test with the two different "shear rates", obtained by operating on the flow rate of the aspiration pump.

The perfusion chamber comprises at least one cytoadhesive substance on the surface thereof or on part thereof. For example, such at least one cytoadhesive substance can be fibrillar type I collagen. Other suitable cytoadhesive substances are those described in EP 2 010 903 A1, in particular Collagen type I/III, Collagen type VI, PG-M/versican (vascular), Perlecan Fibronectin, Laminin-1, Vitronectin, Decorin, Biglycane, Fibulin-1, Tenascin-C, Lumican, Thrombospondin-1, emilin or tissue factor.

The cytoadhesive substance in solution is deposited on a surface portion of the perfusion chamber and is left to incubate for a predetermined time, in order to obtain the coating of the surface with the cytoadhesive substance. In preferred embodiments, collagen in solution at a concentration of 0.9-1 mg/ml in a quantity of about 200 μl will be used.

The deposition of the cytoadhesive substance can be carried out with all known methods, for example by drying or deposition with 2D-3D printing techniques.

Step c) is preferably carried out at a temperature of the perfusion chamber of about 37° C., so as to simulate a patient's physiological conditions.

Step d) has the purpose of recording the platelet aggregate and fibrin formation dynamics, which occur at different times. Such a step is carried out by irradiating the sample with light comprising radiation at a wavelength corresponding to the excitation wavelength of the fluorescent probes used and acquiring corresponding fluorescence images at the emission wavelengths of said fluorescent probes.

The method of the invention includes acquiring:

a first set of fluorescence images at the emission wavelength of the fluorescent probe for the platelets in a given period of time;

a second set of fluorescence images at the emission wavelength of the fluorescent probe of the antifibrin antibody for the fibrin in said given period of time.

The apparatus and the operating method of such an apparatus (software) will be described below.

Steps e) and f) are carried out using conventional numerical calculation methods.

From a study carried out on healthy subjects not subjected to anticoagulant or antiplatelet therapy (controls), mean values of the parameters calculated as described above were obtained. "Anticoagulant therapy" refers to a therapy with traditional oral anticoagulants (TAO) or with new oral anticoagulants (NAO), while "antiplatelet therapy" refers to therapy with acetylsalicylic acid (ASA). The data are reported in the following tables I and II.

The data refer to an 8-bit acquisition system.

TABLE I

| | Platelets | | | Fibrin | | |
|---|---|---|---|---|---|---|
| | AUC Area[(1)] [$\times 10^7$] | AUC MGV[(2)] [$\times 10^4$] | AUC ID[(3)] [$\times 10^9$] | AUC Area[(1)] [$\times 10^7$] | AUC MGV[(2)] [$\times 10^4$] | AUC ID[(3)] [$\times 10^9$] |
| TAO | 3.5 | 2.8 | 4.0 | 2.5 | 1.7 | 3.0 |
| NAO | 2.7 | 2.1 | 2.6 | 2.8 | 1.9 | 3.8 |
| ASA | 3.4 | 2.0 | 3.0 | 3.0 | 2.0 | 4.3 |
| controls | 4.4 | 3.0 | 5.4 | 4.7 | 2.7 | 7.0 |

(1)AUC Area = area under the curve of the area curve − step k)
(2)AUC MGV = area under the curve of the fluorescence intensity curve − step k)
(3)AUC ID = Area under the curve of the integrated density curve − step k)

TABLE II

| | Lag Time [s] | F/P Area | F/P MGV | F/P ID |
|---|---|---|---|---|
| TAO | 270.5 | 0.8 | 0.6 | 0.9 |
| NAO | 269.6 | 1.1 | 1.2 | 2.5 |

TABLE II-continued

| | Lag Time [s] | F/P Area | F/P MGV | F/P ID |
|---|---|---|---|---|
| ASA | 267.5 | 1.0 | 1.2 | 2.2 |
| controls | 207.2 | 1.1 | 1.1 | 1.9 |

F/P Area = AUC Area ratio of fibrin to platelets
F/P MGV = AUC MGV ratio of fibrin to platelets
F/P ID = AUC ID ratio of fibrin to platelets Therefore, the invention relates to a method for the ex-vivo evaluation of the effectiveness of an anticoagulant or antiplatelet treatment on a subject who takes one or more of such therapies, which comprises the following steps:

1) dynamic evaluation of the parameters of AUC Area, AUC MGV, AUC ID and Lag Time as previously described on a blood sample of said subject, in which the values of said parameters refer to an 8-bit acquisition system;

2) comparing the values of said parameters calculated in step 1) with reference values, in which if the subject's platelet AUC Area is $<4.4\times10^7$, preferably $<4\times10^7$, and/or if the subject's platelet AUC MGV is $<3.0\times10^4$, preferably < or equal to $2.8\times10^4$, and/or if the subject's platelet AUC ID is $<5.4\times10^9$, preferably $<4.5\times10^9$, and/or if the subject's fibrin AUC Area is $<4.7\times10^7$, preferably $<3.5\times10^7$, and/or if the subject's fibrin AUC MGV is $<2.7\times10^4$, preferably $<2.2\times10^4$, and/or if the subject's fibrin AUC ID is $<7.0\times10^9$, preferably $<6.0\times10^9$, more preferably $<5.0\times10^9$, and/or if the subject's Lag Time is >210 s, then the subject is likely to be under therapy and said therapy has a medium or high probability of being effective.

The invention further relates to a method for the ex-vivo evaluation of the risk of thrombogenesis or coagulation defects in a subject not undergoing drug therapy, which comprises the following steps:

1A) dynamic evaluation of the parameters of AUC Area, AUC MGV, AUC ID and Lag Time as previously described on a blood sample of said subject, in which the values of said parameters refer to an 8-bit acquisition system;

2A) comparing the values of said parameters calculated in step 1A) with reference values, in which if the subject's platelet AUC Area is $<4.4\times10^7$, preferably $<4\times10^7$, and/or if the subject's platelet AUC MGV is $<3.0\times10^4$, preferably < or equal to $2.8\times10^4$, and/or if the subject's platelet AUC ID is $<5.4\times10^9$, preferably $<4.5\times10^9$, and/or if the subject's fibrin AUC Area is $<4.7\times10^7$, preferably $<3.5\times10^7$, and/or if the subject's fibrin AUC MGV is $<2.7\times10^4$, preferably $<2.2\times10^4$, and/or if the subject's fibrin AUC ID is $<7.0\times10^9$, preferably $<6.0\times10^9$, more preferably $<5.0\times10^9$, and/or if the subject's Lag Time is >210 s, then said subject has a medium or high risk probability of blood coagulation defects;

or:

if the subject's platelet AUC Area is $>4.4\times10^7$, preferably $>5\times10^7$, and/or if the subject's platelet AUC MGV is $>3.0\times10^4$, preferably $>4\times10^4$, and/or if the subject's platelet AUC ID is >$5.4\times10^9$, preferably >$6\times10^9$, and/or if the subject's fibrin AUC Area is >$4.7\times10^7$, preferably >$6\times10^7$, and/or if the subject's fibrin AUC MGV is >$2.7\times10^4$, preferably >$3.5\times10^4$, and/or if the subject's fibrin AUC ID is >$7.0\times10^9$, preferably >$8\times10^9$, and/or if the subject's Lag Time is <210 s, preferably <190 s, then said subject has a medium or high risk probability of thrombogenesis.

Another aspect of the invention is an apparatus for analyzing the coagulation function of a subject's blood sample usable for the evaluation method described above.

With reference to FIG. 1, the apparatus for analyzing the coagulation function of a subject's blood sample, indicated as a whole with the number 1, comprises:

a cartridge 4 comprising a perfusion chamber 5 for the blood sample;

a unit 2 for acquiring fluorescence images of the blood sample;

a movable support member 3 for the cartridge 4;

a unit 6 for moving the reagents, i.e., the solutions of fluorescent probes and blood recalcification or the single reagent which brings them together, and the blood sample;

a system 8 for pumping the blood sample through the perfusion chamber 5.

The components of the apparatus 1 described above are preferably contained in a frame 9, which can be open, i.e., consisting only of the peripheral frame, or closed at least on five sides to form a container or cabinet, and which has a side 9*a* for operator access.

In the following description, the following axes are defined:

y axis relative to a direction which runs between the side 9*a* for accessing the apparatus 1 and the opposite side;

x axis relative to an orthogonal direction with respect to the y axis in a horizontal plane of the apparatus 1;

z axis relative to a direction orthogonal to the plane of the x, y axes.

The terms "x axis", "y axis" and "z axis" refer to the axes shown in FIG. 1 and all the axes parallel thereto.

The movable support member 3 comprises a casing 22 for the cartridge 4, a first support 11, configured to contain a plurality of tips P for a pipette, and a second support member 12 configured to contain two or more containers C, typically tubes for the reagents or the single reagent and for the blood sample.

The support member 3 slides on a guide 41 along the y axis between the following positions:

a retracted position, near the side 9*a* of the frame 9, to allow an operator to load tips P, reagents and blood sample;

at least a first intermediate position, in which the first support 11 of the tips P is aligned along the x axis with the movement unit 6;

at least a second intermediate position, in which the second support 12 of the reagent and blood sample containers C is aligned along the x axis with the movement unit 6;

at least one advanced position, in which the perfusion chamber 5 of the cartridge 4 is aligned along the z axis with the image acquisition unit 2.

The movement of the support member 3 occurs by means of a suitable motorization which causes the rotation of a worm screw acting on the support member 3 causing it to move forward or backward along the y axis. The motorization can be for example a brushless motor.

Figure 13:
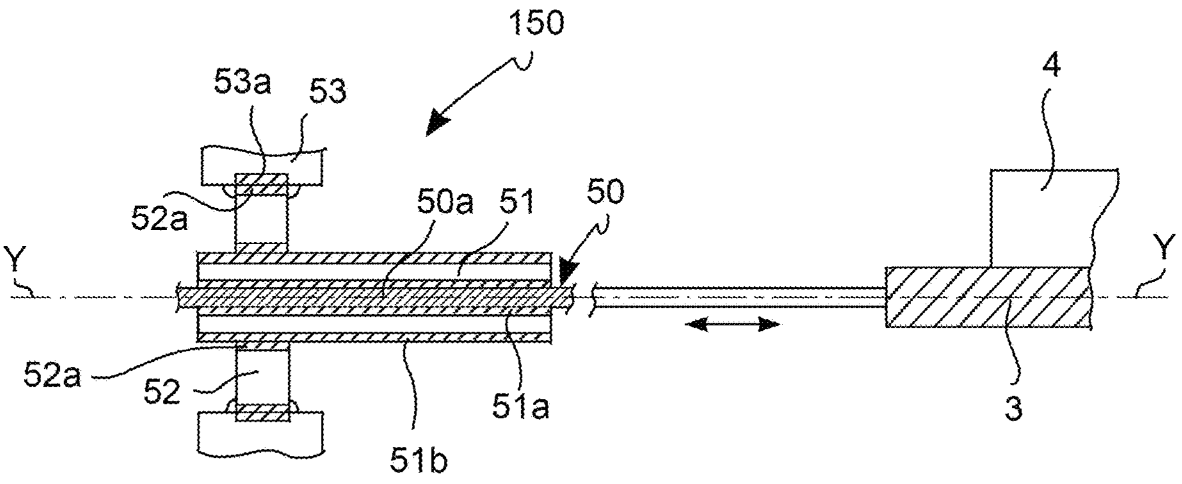
FIG. 13 depicts a lateral schematic view of a system for micrometric adjustment of the position of the cartridge support member.

In certain embodiments, with reference to FIG. 13, the support member 3 can comprise a micrometric adjustment system 150. In such an embodiment, the support member 3, sliding along the guide 41 (omitted for simplification from FIG. 13), can be coupled to a threaded bar 50 provided with a micrometric adjustment system of the displacement along the y axis. For example, the threaded bar 50, fastened to the support member 3, can comprise a fine adjustment screw 51 with a central hole provided with an internal thread 51*a* adapted to engage the corresponding external thread 50*a* of the threaded bar 50, so that a rotation of the fine adjustment screw 51 with respect to the threaded rod 50 produces a first translational movement of the threaded rod 50, and thus of the support member 3, with respect to the fine adjustment screw 51 along the y axis. The fine adjustment screw 51 is also rotatably connected around the y axis, by an external thread 51*b*, to a rotatable element 52 in turn comprising a coarse external thread 52*a*. The rotating element 52 is coupled with a coarse internal thread 53*a* of a fixed element 53, fastened for example on the guide 41 or on the frame 9. Thereby, rotating the rotating element 52 and preventing the rotation of the fine adjustment screw 51, a fast advancement of the threaded bar 50, and therefore of the support member 3, is obtained along the y axis, thus obtaining a coarse adjustment of the position thereof; vice versa, the rotation of the fine adjustment screw 51 produces a translational movement of the fine adjustment screw 51 with respect to the rotatable element 52 along the y axis and an overall micrometric translational movement of the threaded rod 50, and therefore of the support member 3, both with respect to the rotating element 52 and to the fine adjustment screw 51 which is the sum of said translational movements. The fine adjustment screw 51 thus forms a differential screw.

When the rotating element 52 is rotated, appropriate locking means make the rotating element 52 integral in rotation with the fine adjustment screw 51.

This type of mechanism is illustrated for example in the international application published under number WO 2006/057028 A1.

The micrometric adjustment system 150 described above will be moved by an appropriate motorization (not shown) which, as mentioned above, can be a brushless motor or other similar actuator.

The first support 11 for the tips P comprises a plurality of holes 11*a* to house the tips P and a tray portion 11*b* which acts as a collector of the tips P after use, said tray portion 11*b* preferably being placed in an aligned position along the x axis with respect to the holes 11*a* for the tips P.

The second support 12 comprises two or more holes 12*a* for housing the containers C and is aligned along the x axis with respect to the cartridge 4.

The cartridge 4, shown in FIGS. 4, 5 and 6, is housed in the casing 22 (FIG. 3) which has the function of both maintaining the alignment of the cartridge 4 with the cylinder 20*b* of the piston pump 20, and of thermostating the cartridge at a physiological temperature. To this end, the casing 22 comprises two thermocouples and two sensors configured so as to heat the neighborhood of the cartridge 4 to a temperature slightly above physiological temperature and therefore to maintain the blood inside the perfusion chamber 5 at a physiological temperature.

The cartridge 4 comprises a body 23, in the example of an almost cylindrical shape, comprising a flat surface 24. The body 23 unwinds along a longitudinal axis A and is closed at a first end 23*a*, while at the second opposite end 23*b* it comprises a fitting 25 having a seat 25*a* for a syringe pump 20.

The flat surface 24 comprises a groove 26 which, together with a slide 24*a* (FIG. 12), defines the perfusion chamber 5. The surface of the slide 24*a* facing the groove 26 comprises the surface portion of the perfusion chamber 5 comprising the cytoadhesive substance, as described above.

Figure 12:
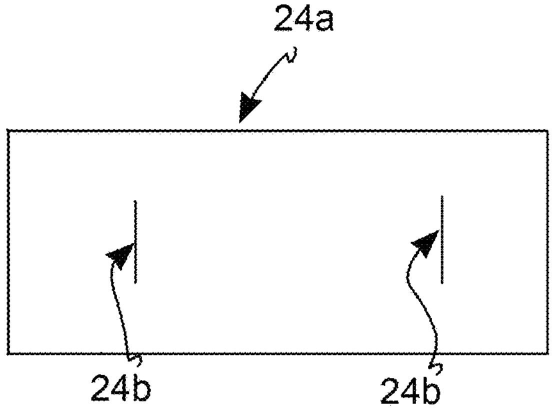
FIG. 12 depicts a schematic plan view of a slide for the perfusion chamber of the invention.

The analytical device comprises reference marks configured so as to identify the height at which the surface is located on which the adhesion phenomenon of the platelets and fibrin will occur. For example, the slide comprises two reference marks 24*b*, for example incisions, to facilitate the focusing of the image acquisition unit 2. The positioning of such reference marks 24*b* shown in FIG. 12 is not indicative of the actual positioning, which will depend on the image acquisition positions which will be defined.

The perfusion chamber 5 has an elongated shape and has a first end 5*a* and a second end 5*b*.

The cartridge 4 further comprises, in a contiguous position to the first end 5*a* of the perfusion chamber 5, a well 27 for loading the blood sample.

The well 27 has a substantially flared upward shape and comprises, at the bottom 27*a*, an inclined ascending microchannel 28 which opens at the first end 5*a* of the perfusion chamber 5.

At the second end 5*b*, the perfusion chamber 5 is instead connected to an inclined descending microchannel 29 which opens into a duct 30 which in turn opens in the seat 25*a* of the fitting 25.

The arrangement of the two inclined microchannels 28, 29 with respectively ascending and descending slope optimizes the flow of the blood sample, reducing the risk of bubble formation and undesired platelet activation.

The term "inclined ascending microchannel" or "inclined descending microchannel" indicates a microchannel having a certain inclination, straight or curvilinear, different from a step profile.

The aspiration flow rate of the pumping system 8, together with the width of the perfusion chamber 5, determines the shear rate to which the blood sample is subjected inside the perfusion chamber 5, as defined previously. In other words, the shear rate can be modulated by modifying the width of the perfusion chamber 5, by modifying the flow rate of the pumping system 8 or by acting on both.

Figure 3:
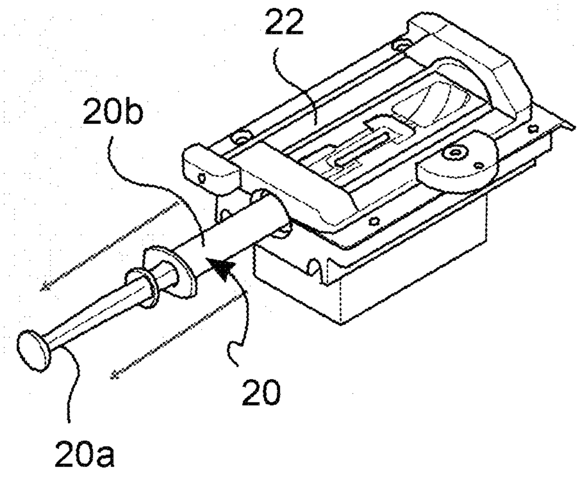
FIG. 3 depicts a perspective view of a second detail of the apparatus of the invention.

The pumping system 8 comprises, in the example described, a syringe pump 20, comprising a plunger 20*a* and a cylinder 20*b*, connected to the cartridge 4 and an actuation member 21 (shown only partially in FIG. 1) which couples the plunger 20*a* of the syringe pump 20 and applies a traction motion thereto indicated by the arrows of FIG. 3, according to a predefined motion law and dictated by the predefined flow parameters inside the perfusion chamber 5 and on which the shear applied to the analyzed blood will depend.

In a different embodiment, shown in FIG. 7, the perfusion chamber 105 has an elongated shape and comprises a first end 105*a*, connected with the inclined ascending microchannel 28, and a second end 105*b*, connected with the inclined descending microchannel 29. The perfusion chamber 105 is divided into two half-chambers 131, 132 by a partition 133 which has a wedge-shaped profile 134 at the first end 105*a*. The two half-chambers 131, 132 have a different width d, D, so that, by maintaining the same blood flow rate, two different shears can be obtained. The size of the half-chambers 131, 132 will in particular be designed so as to obtain, for a certain blood flow rate, the desired shear rates.

Figure 8:
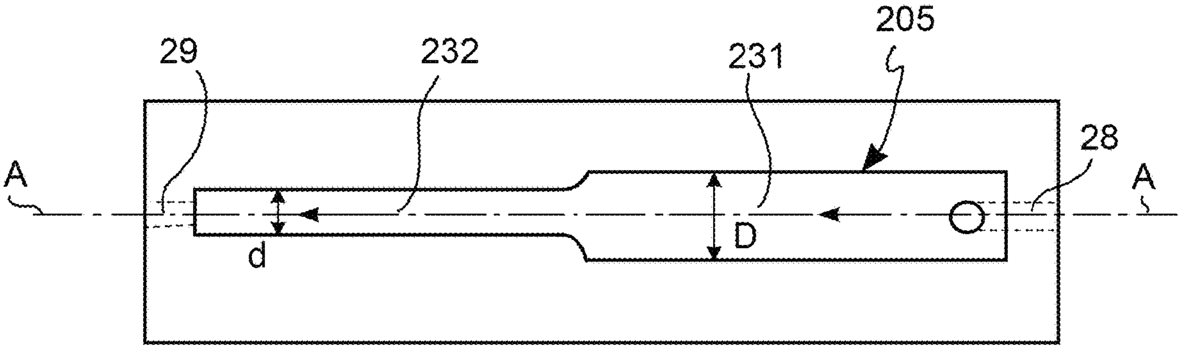
FIG. 8 depicts a schematic plan view of a different embodiment of the perfusion chamber of the cartridge of FIG. 4.

FIG. 8 shows a still different embodiment of the perfusion chamber, here indicated with the number 205.

The perfusion chamber 205 develops along the axis A and has along said axis in series a first half-chamber 231 having width D and a second half-chamber 232 having width d different from width D. In FIG. 8, the half-chamber 231 having the greater width D has been placed upstream of the half-chamber 232 of smaller width d, but in a variant the two half-chambers 231, 232 can be inverted. In this case as well, by maintaining the same blood flow rate, two different shears can be obtained. The size of the half-chambers 231, 232 will in particular be designed so as to obtain, for a certain blood flow rate, the desired shear rates.

Figure 10:
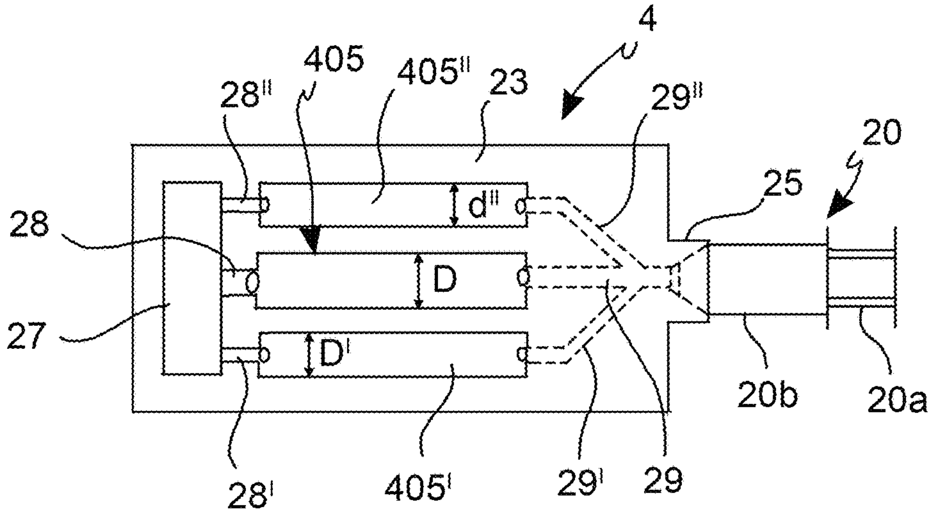
FIG. 10 depicts a schematic plan view of a different embodiment of the cartridge of the invention.

FIG. 10 shows still a different embodiment of the cartridge 4.

The cartridge always comprises a body 23 closed at one end and comprising at the opposite end a fitting 25 for a syringe pump 20, which is shown already coupled to the cartridge 4 so as to form a whole.

The cartridge 4 in this embodiment comprises a plurality of perfusion chambers 405, 405', 405". The centrally positioned perfusion chamber 405 has a width D which can be the same or different from one or both of the other perfusion chambers 405', 405".

The other two perfusion chambers 405', 405" are placed on the two sides of the chamber 405 and are designed with different widths, i.e., the chamber 405' has a width D' greater than the width d" of the chamber 405". However, in other embodiments the two chambers 405', 405" could have equal width.

In certain embodiments, the central perfusion chamber 405 and/or one or both of the lateral perfusion chambers 405', 405" can be divided by a partition as shown in FIG. 7.

Respective ascending microchannels 28, 28', 28" connect the well 27 with the perfusion chambers 405, 405', 405"; respective descending microchannels 29, 29', 29" connect the perfusion chambers 405, 405', 405" with the fitting 25 and thus with the syringe pump 20.

This embodiment of a multi-chamber cartridge 4 allows the simultaneous analysis of a blood sample both in different shear conditions (by virtue of the different width of the chambers), and in relation to different types of corpuscular aggregates, obtainable by coating different portions of the slide 24*a*, at the chambers 405, 405', 405", with different reactive substances, as defined below.

Figure 11:
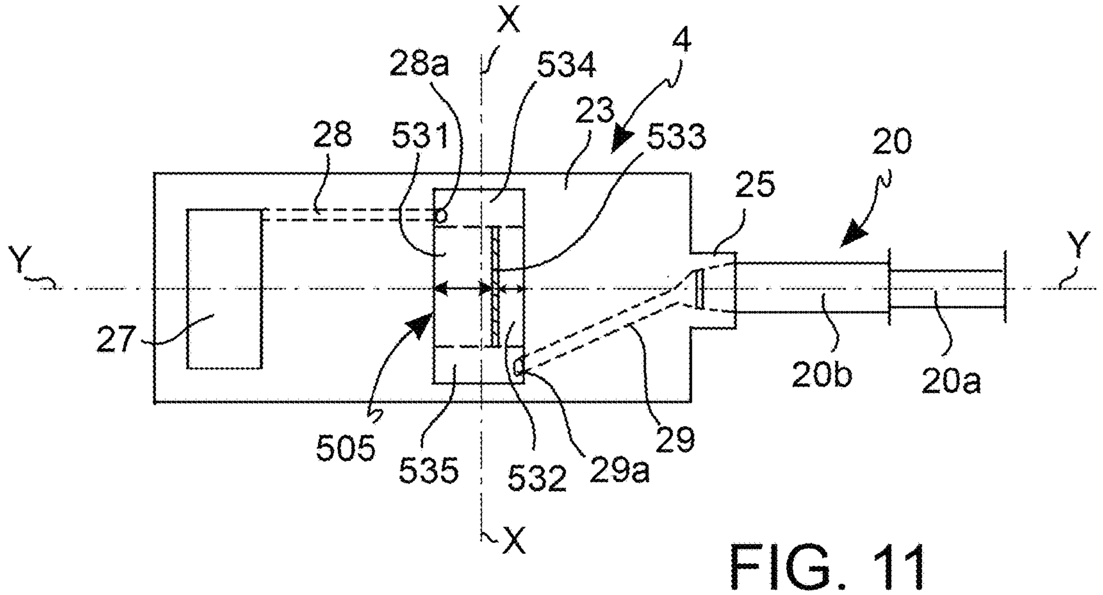
FIG. 11 depicts a schematic plan view of a still different embodiment of the cartridge of the invention.

FIG. 11 shows another embodiment of the cartridge 4.

The cartridge always comprises a body 23 closed at one end and comprising at the opposite end a fitting 25 for a syringe pump 20, which is shown already coupled to the cartridge 4 so as to form a whole.

The perfusion chamber 505 is divided into two half-chambers 531, 532 by a partition 533, as in the embodiment of FIG. 7. In this case as well, a first half-chamber 531 has a width D greater than the width d of the second half-chamber 532. However, in other variants the two half-chambers 531, 532 can have the same width, but portions of the slide 24*b* can be coated at said half-chambers 531, 532 with different reactive substances, as described below.

The perfusion chamber 505 further comprises an accumulation tank 534, placed upstream of the half-chambers 531, 532, and a collection tank 535 placed downstream of the half-chambers 531, 532.

An inclined ascending microchannel 28 connects the well 27 with the accumulation tank 534, while the inclined descending microchannel 29 connects the collection tank 535 with the fitting 25 and thus with the syringe pump 20.

The accumulation tank 534 and the collection tank 535 have a greater depth than the half-chambers 531, 532 and have the function of avoiding preferential lanes for the flow of blood in one of the two half-chambers 531, 532.

In certain embodiments, the tanks 534, 535 can be omitted and the inclined ascending 28 and descending microchannels 29 can have corresponding inlet 28*a* and outlet 29*a* openings placed at the two ends of the chamber 505 at half the width D.

The perfusion chamber 505 is placed in a transverse position, i.e., along an x axis, with respect to the y axis of the cartridge 4 which corresponds to the movement direction of the support member 3 during the analysis. This allows analyzing the corpuscular aggregates in the two half-chambers 531, 532 only by arranging a micrometric movement along the y axis, but making it unnecessary to move along the x axis of the cartridge 4 or of the image acquisition unit 2.

The reagent movement unit 6 comprises an automatic pipettor 10.

The automatic pipettor 10 is movable along two orthogonal axes x and z, so as to be able to move between various positions along the x axis and to be able to raise or lower the movable body 10*a* of the automatic pipettor 10 when necessary. In particular, the automatic pipettor 10 is movable between a position for withdrawing tips P at the movable support 11 or for withdrawing the reagents or blood sample from the respective containers C at the support 12, a position for releasing said reagents at the well 27 of the cartridge 4 and a release position of the used tips P in the tray portion 11*b* of the first support 11. The sequence of such movements includes the following steps:

- withdrawing a new tip P for each reagent, single reagent or blood sample
- withdrawing a reagent or single reagent
- releasing the reagent or the single reagent in the well 27
- releasing the used tip P in the tray portion 11*b* of the first support 11
- withdrawing the blood sample
- releasing the blood sample in the well 27
- releasing the used tip P in the tray portion 11*b* of the first support 11.

The blood sample and reagent withdrawal sequences can also be reversed.

In such an operating sequence, the positioning of the automatic pipettor 10 at the various positions occurs by means of a combined movement of the pipettor 10 along the x and z axes and of the support member 3 along the y axis.

Both the withdrawal of the tips P and the reagents/blood sample from the containers C, as well as the release of the reagents/blood sample, occurs by virtue of a movement along the z axis of the movable body 10*a* of the pipettor. The withdrawal operations occur by virtue of pressure sensors associated with the free end of the movable body 10*a* of the automatic pipettor 10. In particular, the pressure sensor used in the reagent withdrawal step is adapted to detect contact with the liquid surface. This is useful because, as the analysis proceeds, the reagent tube tends to empty and thus the liquid level drops. The stroke of the movable body 10*a* along the z axis is then adjusted by means of this pressure sensor, so that the risk of not withdrawing the solution is avoided.

The automatic pipettor 10 can be for example an automatic pipettor produced by HAMILTON LABORATORIES, mod ZEUS.

Figure 2:
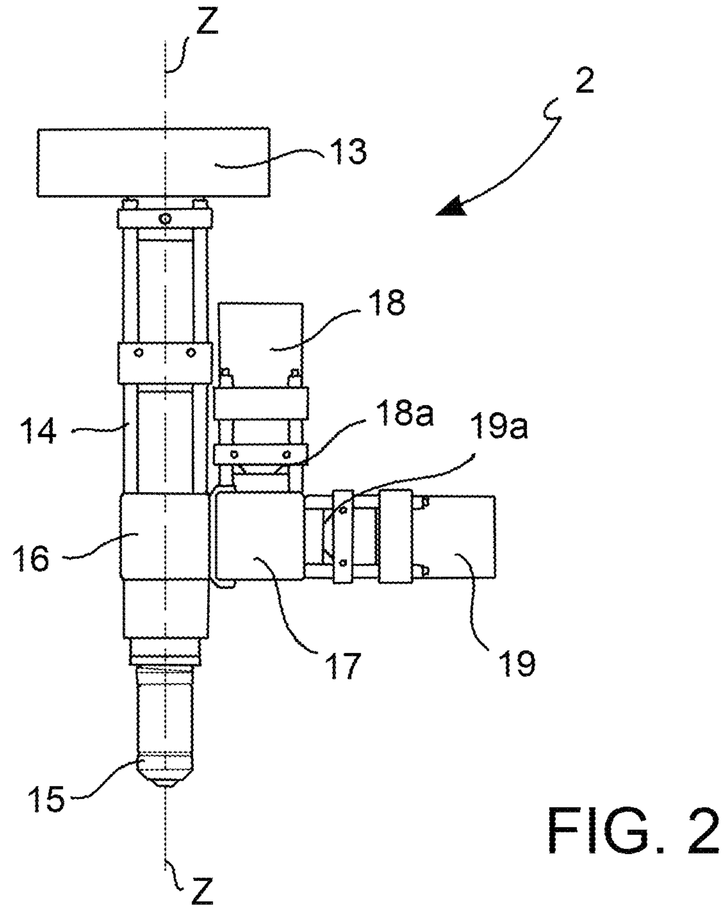
FIG. 2 depicts a front view of a first detail of the apparatus of the invention.

As shown in FIG. 2, the fluorescence image acquisition unit 2 comprises a digital image acquisition device 13, typically a CCD video camera, capable of acquiring gray-scale images, so that a first series of fluorescence images can be obtained, in the form of a close-up sequence of images or video, for the formation of a platelet aggregate over time and a second series of fluorescence images for the fibrin formation over time.

The digital image acquisition device 13 is visually connected, by means of an optical path 14, to a lens 15 which, in operating conditions, is aligned with the perfusion chamber 5 or with a selected portion thereof in which the formation of an aggregate is to be observed.

The lens 15 is movable along the Z axis by means of an actuator (not shown).

A first dichroic filter 16 is arranged along the optical path 14. Laterally with respect to the optical path 14 and at the first dichroic filter 16, there is a second dichroic filter 17 onto which the light radiations of a first light emitter 18 and of a second light emitter 19 converge, which emit light at predefined wavelengths, in particular for the excitation of the platelet probe and that of the fibrin. In preferred embodiments, both the first and the second light emitters 18, 19 are LED emitters.

In particular, the first light emitter 18 and the second light emitter 19 are placed on two faces of the second dichroic filter 17 placed at 90°. It must be understood that such an arrangement is motivated by space requirements and the convenience of access to the instrumentation, so that it can be modified at will to meet different construction requirements.

Respective band-pass filters 18*a*, 19*a* are placed between said light emitters 18, 19 and the second dichroic filter 17.

Thereby, substantially monochromatic light beams are obtained which are able to excite the fluorescent probes present in the sample under examination with the due excitation energy.

The light emitters 18, 19 operate out of phase and preferably in stroboscopic mode so that, when the first emitter 18 emits a light beam, the second emitter 19 is off (or at zero power) and vice versa. Thereby the digital image acquisition device 13 can alternatively acquire an image at a first emission wavelength on a first channel and an image at a second emission wavelength on a second channel. The stroboscopic mode further allows to minimize the light energy delivered to the blood sample, avoiding damage thereof.

In preferred embodiments, as noted above, the first excitation wavelength is about 500 nm (filtered at 480 nm) and the second excitation wavelength is about 550 nm (filtered at 546 nm), while the first emission wavelength is about 510 nm and the second emission wavelength is about 556 nm.

The digital image acquisition unit 2 preferably is or comprises a confocal microscope.

In certain embodiments, the image acquisition unit 2 is movable parallel to the x axis of FIG. 1 along a guide (not shown). This embodiment is particularly useful if using a perfusion chamber 105 (FIG. 7) or a multi-chamber cartridge 4 (FIG. 10) as described above.

Figure 14:
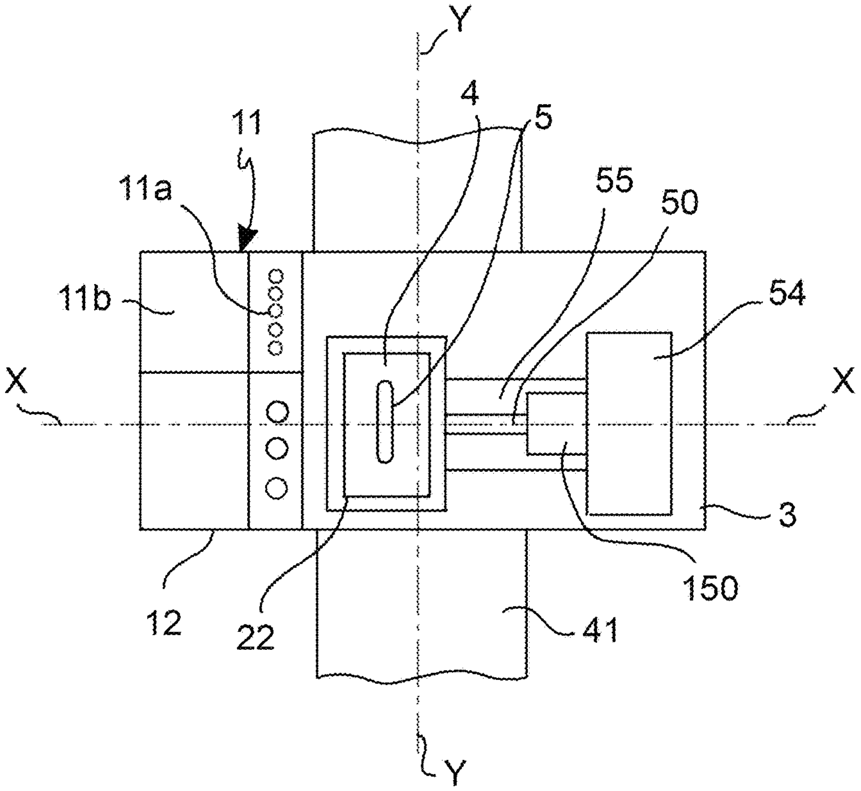
FIG. 14 depicts a schematic plan view of a micrometric adjustment system of the position of the cartridge.

Alternatively, the acquisition unit 2 is fixed, while the cartridge 4 is movable along an x axis. In such an embodiment, shown diagrammatically in FIG. 14, the casing 22 containing the cartridge 4 slides along an x axis on a guide 55 placed on the support member 3 along a transverse direction (parallel to the x axis).

The micrometric movement of the casing 22 along said x axis can occur for example by means of the micrometric adjustment system 150 described in relation to FIG. 13, which can be connected to an actuator 54, for example a brushless motor or the like. In such a case, since the coarse adjustment of the position of the casing 22 is not strictly necessary, the system 150 can also be simplified, eliminating the rotating element 52 and directly coupling the fine adjustment screw 51 with the fixed element 53, by means of appropriate calibration of the respective threads. An example of such a system is shown in FIG. 1 of the international application published under number WO 2006/057028 A1.

A similar micrometric adjustment system can also be adopted for the movement of the image acquisition unit 2 along the x axis.

Figure 9:
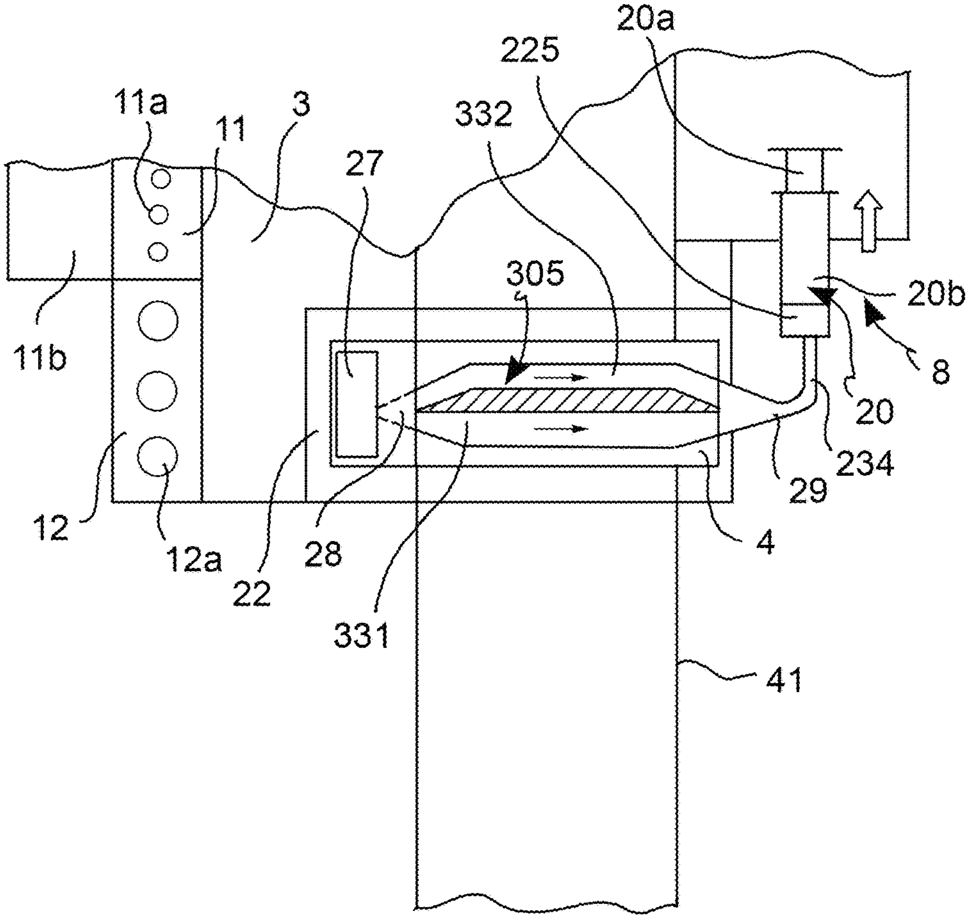
FIG. 9 depicts a schematic plan view of a different embodiment of the movable support member.

FIG. 9 instead shows a different embodiment of the movable support member 3. In such an embodiment, the cartridge 4 is arranged transversely, i.e., along an x axis, and comprises a perfusion chamber 305 comprising a first half-chamber 331 and a second half-chamber 332, said half-chambers 331, 332 being placed in parallel. The microchannel 29 placed downstream of the perfusion chamber 305 continues in a rigid or flexible tube 234 which is arranged as a rounded elbow and ends with a fitting 225 for the cylinder 20*b* of the syringe pump 20. Therefore, in such an embodiment, the actuation member 21 of the syringe pump 20 is placed in an offset position with respect to the guide 41.

Furthermore, this embodiment avoids the arrangement of a movement of the image acquisition unit 2 or of the cartridge 4 along an x axis. In fact, the acquisition of images at the two half-chambers 331, 332 can be done by means of a micrometric displacement of the support member 3 along the guide 41.

The micrometric movement of the cartridge 4 along the y axis, as necessary for the embodiments of FIG. 8, of FIG. 9 and of FIG. 11, or along the x axis, as necessary for the embodiments of FIG. 7 and of FIG. 10, or, in the latter two cases, of the image acquisition unit 2 along the x axis, becomes essential due to the limited spatial separation between said half-chambers 131, 132 or 231, 232 or 331, 332 or 431, 432, 405', 405" or 531, 532 and due to the need to acquire images in a repeated and repeatable manner.

In the previous description, the double half-chambers have been illustrated in relation to the performance of experiments with different shears, which requires, for the same blood flow rate, a different width of the half-chambers. However, as previously mentioned, it will be possible to arrange two or more half-chambers, or a multi-chamber cartridge 4, even of equal width, but comprising a wall or a portion of the slide with different reactive substances, in order to observe the formation of aggregates of different nature, by marking compounds such as phosphatidylserine, P-selectin, fibrinogen and derivatives thereof, thrombin, allb33, von Willebrand factor, thrombospondin-1, Factor V, Factor XII, Factor VIII, Fetor IX, Factor X, dendritic cells, differentiated and undifferentiated, tumor antigens, tumor lysates, leukocytes, immature granulocytes, hematopoietic progenitor cells, erythroblasts, red blood cells, tissue factor, platelet antigens, etc.

The cartridge 4 is of the disposable type and can form a kit together with the syringe pump 20, or parts thereof, of the disposable type as well. In such a kit, the cartridge 4 and the syringe pump 20 can be in a pre-assembled condition. In certain embodiments, the syringe pump 20 can also be non-removably fastened to the fitting 25.

The kit can further contain tubes sealed with the reagents or a tube sealed with the single reagent and optionally one or more slides 24*a* pretreated with the cytoadhesive substance and/or with other reactive substances, optionally in different and discrete portions of the slide 24*a*, and optionally comprising two or more reference marks, for example incisions. The slides can comprise, on the surface treated with the cytoadhesive substance, a removable protective film or they can already be coupled with the cartridge 4.

The apparatuses 1 described here above can be operated automatically by a command and control unit by means of a program comprising the following steps:

I) preparing the blood sample,

II) conducting the dynamic analysis,

III) processing the fluorescence images acquired in the dynamic analysis.

Step I) comprises the following steps:

Automatic focusing procedure on two incisions present on the slide in order to accurately identify the height at which the lower surface of the slide is located on which the adhesion phenomenon of the platelets will occur. Such a focus is functional to the correct vertical positioning of the lens.

Collecting a known volume of reagents or single reagent and dispensing it in the well 27, for example by means of a pipettor.

Collecting a known volume of blood and dispensing it in the well 27, for example by means of a pipettor.

Step II) comprises the following steps:

IIa) Aspirating the mixture of blood and reagents or single reagent inside the perfusion channel of the cartridge by means of a syringe pump with a defined speed for a fixed time interval. It should be emphasized that the shape of the channel or the presence of multiple channels or multiple parts of a channel can imply the creation of different shears. In the case of a channel with a homogeneous width opening, the pumping system 8 can be activated with a predefined flow rate as a function of the desired shear rate;

IIb) initializing the blood sample analysis procedure;

IIc) acquiring fluorescence images of the blood sample under dynamic conditions.

Step IIb) includes focusing on the area of the perfusion chamber 5 on which the platelets adhere.

The focusing operation of the area of the perfusion chamber 5 on which the platelets adhere is preferably carried out in autofocus mode, according to conventional procedures in the digital image acquisition field, and allows identifying the plane along the Z axis on which the adhesion of the platelets occurs.

The acquisition area can be single or, as previously mentioned in relation to the arrangement of two or more perfusion half-chambers, multiple areas can be identified with different distances from the entry point of the blood sample in the perfusion chamber (in the case of half-chambers in sequence, FIG. 8) or in a different position along an x axis (in the case of chambers or half-chambers in parallel, FIGS. 7, 9, 10) or along a y axis (in the case of half-chambers in parallel with cartridge arranged transversely, FIG. 11).

Step IIc) comprises the following operations:

turning on the first light emitter 18 for a first predetermined period of time to irradiate the blood sample with light at a first wavelength corresponding to the excitation wavelength of the fluorescent platelet probe, and during said first time period, acquiring a first fluorescence image at a first emission wavelength characteristic of the fluorescent platelet probe;

turning on the second light emitter 19 for a second predetermined period of time to irradiate the blood sample with light at a second wavelength corresponding to the excitation wavelength of the fluorescent fibrin probe, and during said second time period, acquiring a first fluorescence image at a second emission wavelength characteristic of the fluorescent fibrin probe;

repeating the two preceding operations in sequence for a preset number of times, so as to acquire a first series of fluorescence images at said first emission wavelength characteristic of the fluorescent platelet probe and a second series of fluorescence images at said second emission wavelength characteristic of the fluorescent fibrin probe, wherein each image corresponds to an acquisition time t with respect to the time to.

Step III) comprises the following steps (such steps could be different in sequence or numerical parameter value for the series of images acquired for platelets and that acquired for fibrin):

IIIa) Binarizing the images by means of an algorithm (e.g., Niblack) with parameters which differentiate the signal of interest with respect to the background (e.g., optimal radius for the resolution of small objects=30 and optimal radius for the resolution of large objects=60), so as to create a set of illuminated pixels and a set of dark pixels;

IIIb) Summing the images resulting from step IIIa) to obtain the resolution of objects of various size in a single series of images;

IIIc) Eliminating the spurious signals, represented by small areas of brightness less than 2 illuminated pixels, from the resulting series of images;

IIId) Inverting the value of each pixel to create a mask to be subtracted from the original image;

and wherein step III further comprises at least one of the following steps:

IIIe) creating a first curve of area covered by illuminated pixels vs. time (t) for the formation of a platelet aggregate and a second curve of area covered by illuminated pixels vs. time for the fibrin formation;

IIIf) creating a first curve of average fluorescence intensity vs. time for the formation of platelet aggregate and a second curve of average fluorescence intensity vs. time for the fibrin formation;

IIIg) creating a first integrated density curve defined as the product of area and fluorescence intensity vs. time for the formation of the platelet aggregate and a second integrated density curve defined as the product of area and fluorescence intensity vs. time for the fibrin formation;

IIIh) creating a curve of particle number vs. time, in which the number of particles is given by the number of platelet aggregates consisting of more than 2 illuminated pixels;

IIIi) creating a curve of particle size vs. time, in which the particle size is given by the average size of the platelet aggregates consisting of more than 2 illuminated pixels;

IIIj) calculating a lag time value representing the fibrin formation time defined as the time corresponding to the first occurrence of five consecutive images in which the value of the measured area related to fibrin is >1% of the maximum peak value of the curve;

IIIk) calculating the AUC (Area Under the Curve) values given by the area under the curve of the parameter obtained in said at least one step e), f), g), h) and i);

IIIl) calculating values of maximum slope, defined as the relative maximum points of the first derivative function calculated for the curves of the parameter obtained in said at least one step e), f), g), h) and i);

IIIm) calculating values of maximum acceleration, defined as the relative maximum points of the second derivative function calculated for the curves of the parameter obtained in said at least one step e), f), g), h) and i);

IIIn) calculating values of F/P ratio, defined as the ratio of the AUCs of fibrin to the AUCs of the platelets of the parameter obtained in said at least one step e), f) and g).

Lag time is an important parameter, i.e., the instant in which fibrin begins to form, with respect to t0.

In step IIIg) the integrated density ID(t) function represents a surrogate of the volume of aggregates or fibrin formed.

In step IIIh), IIIi) and IIIk), the number, average size and area covered by platelet aggregates or fibrin account for the different biological dynamics of the subject's coagulation. For example, with the same % of covered area, different biological and clinical significance is associated if a small number of large area aggregates or a high number of small area aggregates are detected.

The advantages of the method and the apparatus described above are evident from what has been said.

The method of evaluating the thrombogenic potential of the single individual allows to evaluate diseases related to coagulation defects, to monitor and "adjust" the anti-aggregating or anticoagulant therapy in a personalized manner and to highlight an abnormal thrombogenic risk in patients who do not yet have pathological symptoms. The apparatus described above, together with the operating program of the command and control unit, allows to proceed with the performance of the evaluation method in an automatic, precise and reproducible manner, returning reliable and easily consultable analytical data.

It is apparent that only some particular embodiments of the present invention have been described, to which those skilled in the art will be able to make all the necessary changes for the adaption thereof to particular applications, without departing from the protective scope of the present invention.

For example, although only a syringe pump has been described for moving the sample in the perfusion chamber, it must be clearly understood that any suitable pump or micro-pump can also be used, as is well known to those skilled in the art.

The invention claimed is:

1. A cartridge for conducting a dynamic ex-vivo evaluation method of a coagulation process in a subject's blood sample, comprising at least one perfusion chamber, a well for loading the blood sample and reagents, an inclined ascending microchannel connecting the well to a first end of the perfusion chamber, and an inclined descending microchannel placed at a second end of the perfusion chamber, wherein the cartridge comprises reference marks configured to identify a height at which the surface is located on which an adhesion phenomenon of the platelets and fibrin will occur.

2. The cartridge according to claim 1, wherein said at least one perfusion chamber comprises two half-chambers of different width, placed in series or in parallel, or wherein the cartridge comprises at least two perfusion chambers placed in parallel and wherein at least two of said perfusion chambers have a different width.

3. The cartridge according to claim 1, comprising a fitting for a syringe pump.

4. The cartridge according to claim 1, wherein the at least one perfusion chamber is closed by a glass slide, a surface of the glass slide facing the perfusion chamber comprises a reactive substance.

5. The cartridge according to claim 1, wherein the perfusion chamber has an elongated shape and comprises a first end, connected to the inclined ascending microchannel, and a second end, connected to the inclined descending microchannel, the perfusion chamber being divided into two parallel half-chambers by a dividing partition, the two half-chambers having a different width, so that, by maintaining a same blood flow rate, two different shears are obtainable.

6. The cartridge according to claim 1, wherein the perfusion chamber extends along an axis and has in series along said axis a first half-chamber having a first width and a second half-chamber having a second width different from the first width of the first half-chamber.

7. The cartridge according to claim 1, comprising a plurality of perfusion chambers, wherein a centrally positioned perfusion chamber has a width which is the same or different from the width of one or both of the other perfusion chambers.

8. The cartridge according to claim 7, wherein the central perfusion chamber and/or one or both of the other perfusion chambers are divided into two half-chambers by a separating partition.

9. The cartridge-according to claim 1, wherein the perfusion chamber is placed in a transverse position, along an x axis, with respect to a y axis of the cartridge, the perfusion chamber being divided into two half-chambers by a dividing partition and wherein a first half-chamber has a width equal to or different from the width of the second half-chamber, wherein the perfusion chamber comprises an accumulation tank, placed upstream of the half-chambers, and a collection tank placed downstream of the half-chambers, and wherein the inclined ascending micro-channel connects the well with the accumulation tank, while the inclined descending micro-channel connects the collection tank with a fitting.

10. The cartridge according to claim 1, wherein the glass slide comprises on discrete and predefined portions of the surface facing the at least one perfusion chamber one or more reactive substances chosen from substances adapted to promote the formation of aggregates of different nature, by marking compounds.

11. The cartridge according to claim 10, wherein said one or more reactive substances is chosen from type I fibrillar Collagen, type I/III Collagen, type VI Collagen, PG-M/versican (vascular), Perlecan Fibronectin, Laminin-1, Vitronectin, Decorin, Biglycan, Fibulin-1, Tenascin-C, Lumican, Thrombospondin-1, emilin and tissue factor.

12. A disposable kit comprising at least one cartridge as defined in claim 1 and a syringe pump.

13. The kit according to claim 12, comprising one or more sealed test tubes with the reagents.

14. The cartridge according to claim 1, wherein the perfusion chamber has an elongated shape and comprises a first end, connected to the inclined ascending microchannel, and a second end, connected to the inclined descending microchannel, the perfusion chamber being divided into two parallel half-chambers by a dividing partition which has, at the first end, a wedge profile, the two half-chambers having a different width, so that, by maintaining a same blood flow rate, two different shears are obtainable.

15. The kit according to claim 12, wherein the syringe pump is pre-assembled with the cartridge in a fixed or removable manner.

16. The cartridge according to claim 1, wherein the glass slide comprises on discrete and predefined portions of the surface facing the at least one perfusion chamber one or more reactive substances chosen from substances adapted to promote the formation of aggregates of different nature, by marking compounds selected from the group consisting of: phosphatidylserine, P-selectin, fibrinogen and derivatives thereof, thrombin, allb33, von Willebrand factor, thrombospondin-1, Factor V, Factor XII, Factor VIII, Factor IX, Factor X, differentiated and undifferentiated dendritic cells, tumor antigens, tumor lysates, leukocytes, immature granulocytes, hematopoietic progenitor cells, erythroblasts, red blood cells, tissue factor and platelet antigens.

17. The kit according to claim 12, comprising one or more sealed test tubes with the reagents and one or more glass slides pretreated with the cytoadhesive substance and/or with other reactive substances, in different and discrete portions of the glass slide, and comprising two or more reference marks comprising engravings, wherein the one or more glass slides comprise, on the surface treated with the reactive substance, a removable protective film or a protective film already coupled with the cartridge.

18. The cartridge according to claim 1, wherein the perfusion chamber is placed in a transverse position, along an x axis, with respect to a y axis of the cartridge, the perfusion chamber being divided into two half-chambers by a dividing partition and wherein a first half-chamber has a width equal to or different from the width of the second half-chamber, wherein the perfusion chamber comprises an accumulation tank, placed upstream of the half-chambers, and a collection tank placed downstream of the half-chambers, and wherein the inclined ascending micro-channel connects the well with the accumulation tank, while the inclined descending micro-channel connects the collection tank with a fitting, the accumulation and collection tanks having a greater depth than the half-chambers.

* * * * *